(12) United States Patent
Snyder

(10) Patent No.: US 8,475,511 B2
(45) Date of Patent: Jul. 2, 2013

(54) DEVICE FOR APPLYING COLD THERAPY TO FEET

(76) Inventor: Kenneth C. Snyder, Whitehall, PA (US)

( * ) Notice: Subject to any disclaimer, the term of this patent is extended or adjusted under 35 U.S.C. 154(b) by 221 days.

(21) Appl. No.: 12/984,093

(22) Filed: Jan. 4, 2011

(65) Prior Publication Data

US 2012/0172958 A1 Jul. 5, 2012

(51) Int. Cl.
 *A61F 7/10* (2006.01)
(52) U.S. Cl.
 USPC .............. 607/111; 607/96; 607/108
(58) Field of Classification Search
 USPC ......................................... 607/111
 See application file for complete search history.

(56) References Cited

U.S. PATENT DOCUMENTS

| | | | |
|---|---|---|---|
| 3,889,684 A | 6/1975 | Lebold | |
| 4,055,188 A | 10/1977 | Pelton | |
| 5,016,629 A | 5/1991 | Kanare | |
| 5,069,208 A | 12/1991 | Noppel et al. | |
| 5,921,243 A | 7/1999 | Shakoor | |
| 5,961,544 A * | 10/1999 | Goldman et al. | 607/111 |
| 6,315,786 B1 * | 11/2001 | Smuckler | 606/201 |
| 6,602,216 B1 | 8/2003 | Nordt, III | |
| 6,699,209 B2 | 3/2004 | Turtzo | |
| 6,886,276 B2 | 5/2005 | Hlavac | |
| 7,572,241 B2 | 8/2009 | Slautterback et al. | |
| 7,596,887 B2 | 10/2009 | McClellan | |
| 7,806,841 B2 | 10/2010 | Caselnova | |
| 7,827,703 B2 | 11/2010 | Geer et al. | |
| 2002/0019657 A1 * | 2/2002 | Elkins | 607/111 |
| 2002/0162250 A1 * | 11/2002 | Campbell et al. | 36/166 |
| 2004/0073281 A1 * | 4/2004 | Caselnova | 607/111 |
| 2005/0240139 A1 | 10/2005 | Bushby | |
| 2005/0251073 A1 | 11/2005 | Roth | |
| 2009/0038181 A1 | 2/2009 | Loughnane | |

* cited by examiner

*Primary Examiner* — Linda Dvorak
*Assistant Examiner* — Jared W Pike
(74) *Attorney, Agent, or Firm* — Ceasar, Rivise, Bernstein, Cohen & Pokotilow, Ltd.

(57) ABSTRACT

A device for applying cold therapy to the foot of a wearer is disclosed. The device comprises a foot pad having a pre-molded configuration for directly contacting the bottom of the foot and surrounding heel area. The foot pad includes a heel portion sized to receive and surround the heel of the foot and a raised and contoured arch portion positioned to place localized pressure on the arch of the foot. The entire foot pad is formed of an ice pack that includes a container or shell for receiving and containing a substance capable of maintaining an extremely low temperature for an extended period of time during application to the foot. The device also includes a securement mechanism that is arranged for engaging the foot pad to the bottom of the wearer's foot.

13 Claims, 2 Drawing Sheets

DEVICE FOR APPLYING COLD THERAPY TO FEET

FIELD OF INVENTION

The present invention relates to a device for applying cold therapy to feet. More particularly, this invention relates to a device for treating ailments and inflammations of the foot including plantar fasciitis and tendonitis such as Achilles tendonitis, by applying cold therapy to reduce inflammation in these areas of the foot.

BACKGROUND OF THE INVENTION

As feet bear the weight of the body, foot tendons are also susceptible to many stresses while standing, walking, running, or jumping. If normal motion of the tendon is impaired, the tendon will become inflamed and movement will become painful. This is called tendonitis, and literally means inflammation of the tendon. Common causes of tendon pain are improperly fitting shoes or constant use of high heeled shoes, improper movement of the foot, repetitive sports activity or physical activity or trauma, obesity, aging, flat feet or feet with very high arches, overuse of tendons, diabetes, and rheumatoid arthritis.

Elderly or aged people are mostly affected by foot tendon and ligament pain. However, tendonitis can also be experienced by younger people in case of repeated injury to the tendon because of overuse. Foot tendonitis is commonly found in the Achilles tendon at the ankle joint. The Achilles tendon is the thickest and strongest tendon in the body. The Achilles tendon connects the heel to the muscles of the lower leg. Physicians routinely prescribe the application of ice packs to reduce pain and swelling associated with tendonitis.

The plantar fascia is located in the arch area of the foot and runs across the bottom of the foot from the heel to the ball and spreads out across the width of the foot. The plantar fascia serves as a shock absorber while walking and transfers tensile forces along the bottom of the foot. The plantar fascia serves the vital role of maintaining the shape of the arch of the foot. As tensile stresses are produced in the bottom of the foot, the plantar fascia absorbs the tensile forces and maintains the shape of the foot arch.

For example, while standing or while in motion, forces experienced by the foot tend to flatten the arches. This flattening effect is especially acute in people having high arches. The plantar fascia running along near the bottom surface of the foot is analogous to a string in an archer's bow. Forces that tend to move the ends of the bow apart increase tension on the string. In other words, as forces on the arch push the bones downward, the plantar fascia is subjected to tensile forces. If the tension on the plantar fascia becomes excessive, the plantar fascia may be damaged and produce a condition called plantar fasciitis. Plantar fasciitis is a painful medical condition resulting from inflammation of the plantar fascia. The plantar fascia is thick and essentially inelastic. Overstressing the plantar fascia may produce tears in the plantar fascia or separate the plantar fascia from bone and other surrounding materials. Frequently, the inflamed areas are along the arch of the foot or near the heel of the foot. Plantar fasciitis may be quite debilitating in that everyday activities such as walking and standing may be very painful.

Ice or other types of cold compresses are commonly recommended by physicians for reducing inflammation, especially resulting from high impact activities or from standing still for extended periods of time. Typical treatments for tendonitis of the foot and plantar fasciitis may involve oral anti-inflammatories, ice packs, bedrest, stretching, steroid injections, night splints and wedge-shaped arch supports. In extreme cases, treatment of tendonitis of the foot or plantar fasciitis may require corrective surgery.

For example, treatment for plantar fasciitis may include medical personnel strapping strips of tape to the bottom of an injured foot. Strips of tape are applied at various angles across the bottom of the foot. The tape is difficult to remove from the rolls and bunches up during the taping process. Thus, care must be exercised during the application of the tape to avoid wrinkles in the tape which can cause blisters and other problems. Taping the foot can be cumbersome, inefficient, and ineffective in preventing excessive stretching of the plantar fascia. Additionally, applying and/or attaching an ice pack to the foot may be cumbersome and may require the use of a bandage or other securement means to attach the ice pack to the foot.

Sometimes when current methods of treatment for tendonitis of the foot and plantar fasciitis are ineffective, expensive surgical procedures are required to relieve pain. For example, to obtain access to a tendon of the foot or the plantar fascia, surgeons may perform either an endoscopic procedure requiring small incisions or conventional direct visualization requiring the underside of the foot to be opened up. With either painful procedure, scars may result and recovery time may be from weeks to months.

Even with treatment, improper treatment of tendonitis or plantar fasciitis may lead to other medical problems. For example, improper treatment of plantar fasciitis can lead to "heel spurs." Thus, it is desirable to have a device for treating the pain of tendonitis or plantar fasciitis. It is also desirable to have a device for treating foot inflammations such as tendonitis of the foot and plantar fasciitis that is economical and may be easily applied by the wearer.

SUMMARY OF THE INVENTION

A device for applying cold therapy to the foot of a wearer is disclosed. The device comprises a foot pad having a premolded configuration for directly contacting the bottom of the foot and surrounding heel area. The foot pad includes a heel portion sized to receive and surround the heel of the foot. The foot pad also includes a raised and contoured arch portion positioned to lie beneath and place localized pressure on the arch of the foot where the plantar fascia and tendons of the foot are located. The entire foot pad is formed of an ice pack that includes a container or shell for receiving and containing a substance capable of maintaining an extremely low temperature for an extended period of time during application to the foot. The device also includes a securement mechanism that is arranged for engaging the foot pad to the bottom of the wearer's foot.

DETAILED DESCRIPTION OF THE PREFERRED EMBODIMENTS

Figure 1:
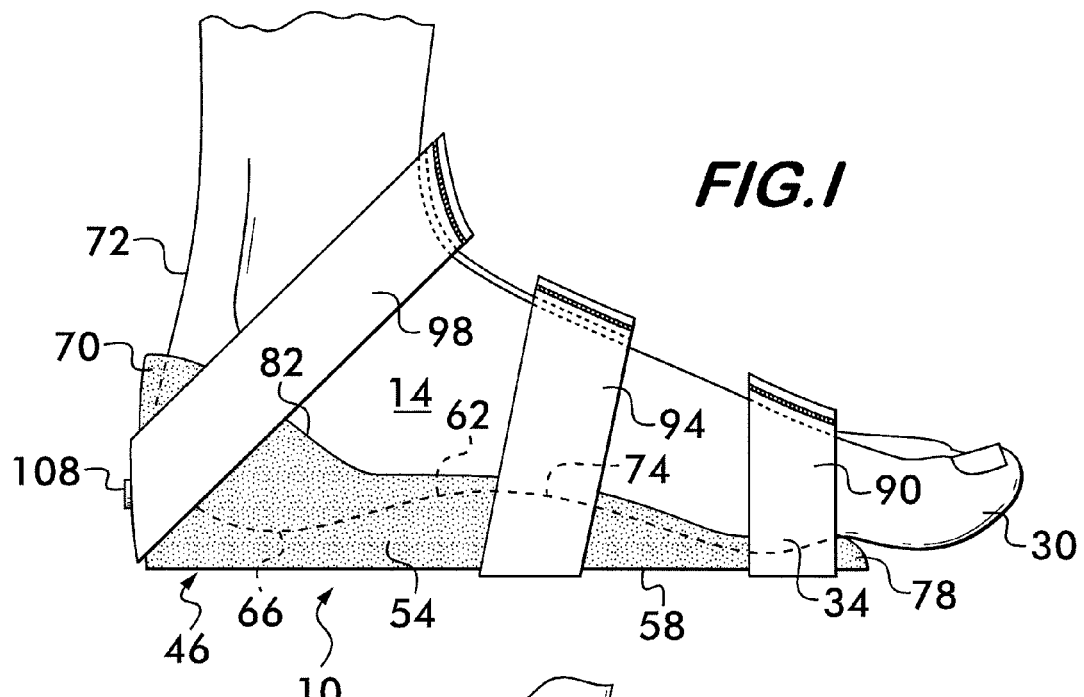
FIG. 1 is a side elevational view of a preferred embodiment of the present invention attached to a foot.

Referring now to FIG. 1, there is shown at 10 a device of the present invention for applying cold therapy to a human foot.

Figure 3:
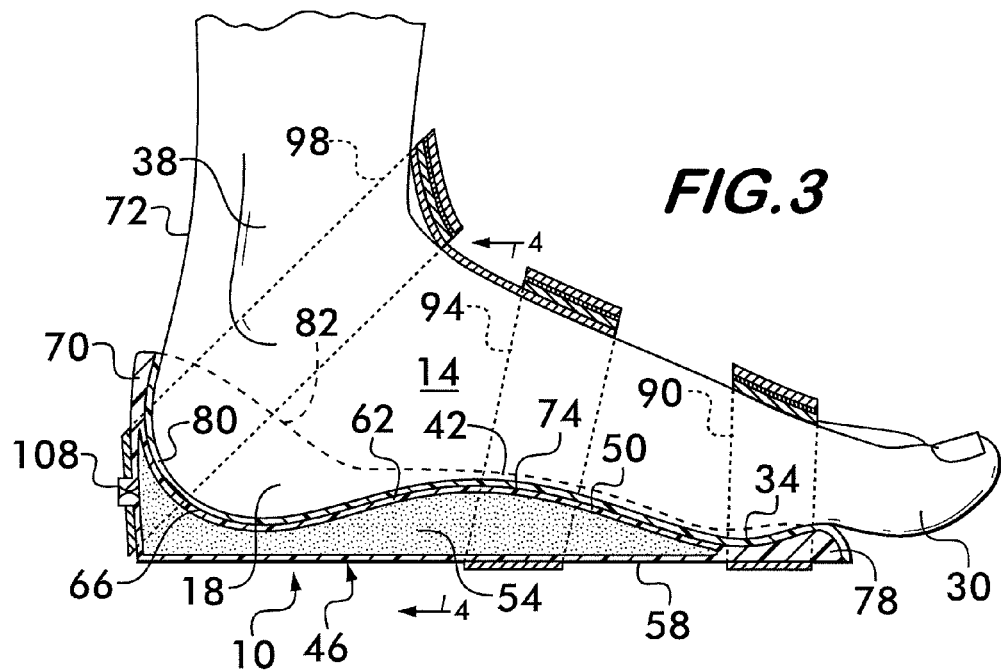
FIG. 3 is a cross-sectional view taken along line 3-3 of FIG. 2.

The longitudinally-extending foot 14 includes a heel 18 (FIG. 3), an inner side 22, an outer side 26, and a plurality of five longitudinally-extending toes 30 extending from a metatarsal joint located in the ball 34 of the foot 14. The foot 14 is connected to an ankle of a leg at the ankle joint 38 disposed above the heel 18 of the foot 14. As best shown in FIG. 3, the foot 14 includes an arch (located in the region indicated at 42) in which the plantar fascia extends. The plantar fascia is attached to the heel bone (calcaneus) located generally at 18 and fans out to attach to the bottom of the metatarsal bones in the region of the ball 34 of the foot.

Figure 4:
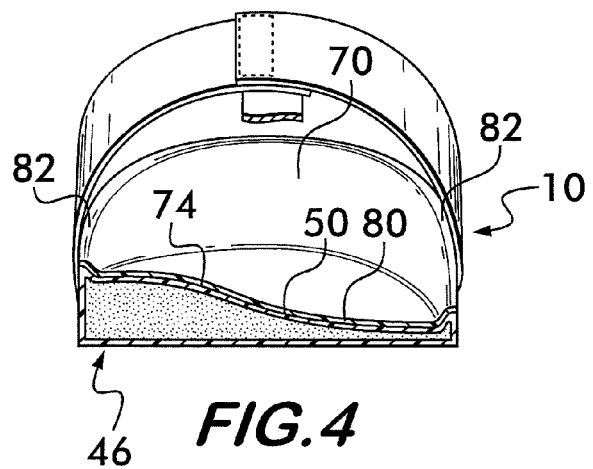
FIG. 4 is a cross-sectional view taken along line 4-4 of FIG. 3.

The device 10 includes a foot pad 46 that takes the form of a reusable freezer pack that has been molded to approximate the contour of the bottom of a wearer's foot. The foot pad 46 shown in the figures is intended for wearing on the left foot. As best shown in FIGS. 1, 3 and 4, the foot pad 46 is formed of a container defined by a thin rigid continuous outer wall 50, the container having an interior cavity for retaining a coolant or refrigerant 54 therein. The outer wall 50 may be formed of any suitable impervious plastic or rubber material and the container may be formed any suitable method, e.g., blow molding. A suitable plastic might be one that is used for a shell of a conventional freezer pack intended for keeping food cold in lunch boxes. The container includes a generally flat bottom portion 58 and an in-built upper foot bed 62 that is contoured to provide support to the foot 14. The foot pad outer wall 50 is formed of any suitable impervious material for containing a coolant or a refrigerant such as a gel or liquid.

As best shown in FIGS. 1 and 3, the foot bed 62 includes a recessed heel cup portion 66 that provides support for the heel 18. A thickened portion 70 is provided that is integral with the recessed heel cup portion 66 and extends upwardly to make contact with the wearer's heel in proximity to the wearer's Achilles' tendon 72. The upper foot bed 62 extends forwardly from the heel cup portion 66 through a contoured arch portion 74 to a front edge 78 located just below the ball 34 of the foot 14. The contoured arch portion 74 is shaped to approximate the contour of the wearer's arch in which the plantar fascia and tendons of the foot are located. In this manner, the foot pad 46 can apply localized pressure and cold therapy to the wearer's heel 18, the foot arch (located in the region indicated at 42), and through the ball 34 of the foot 14.

The front edge 78 is rounded and contoured to eliminate any sharp edges so the wearer can comfortably wear the device 10 on the foot with minimal or no discomfort to the foot or toes. The device is arranged for wearing while the user is off his or her feet. The upper foot bed 62 extends no further than the ball 34 of the foot to prevent the toes 30 from becoming uncomfortably cold during use of the device 10.

Figure 2:
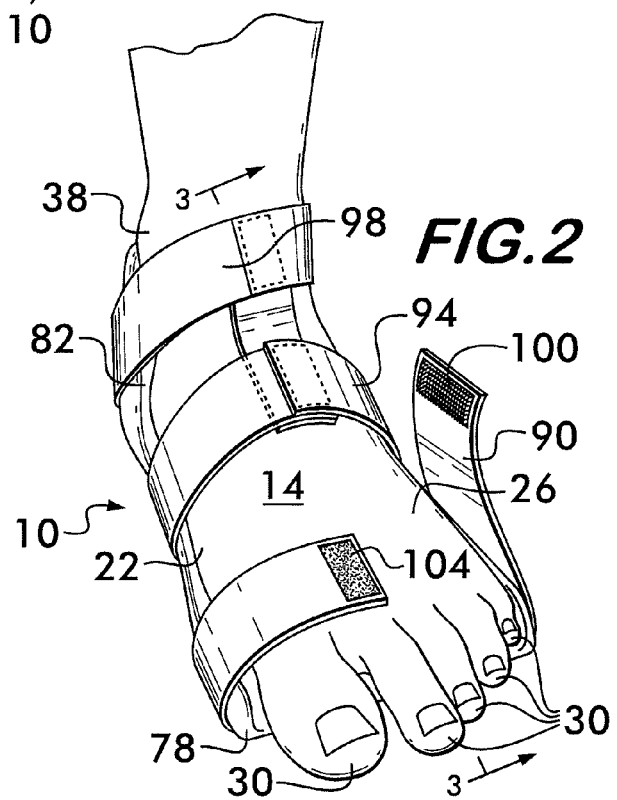
FIG. 2 is an isometric view of a preferred embodiment of the present invention attached to a foot.

It should be understood that the device 10 of the present invention may be designed so that the recessed heel cup portion 66 and contoured arch portion 74 of the upper foot bed 62 are shaped and sized to best suit the contour of the bottom of a foot having a high arch, a low arch, or a flat arch. Likewise, the overall dimensions of the foot pad 46 may be provided in differing lengths and widths to accommodate differences in the length and width of the foot to be treated. As indicated in FIG. 2, the upper foot bed 62 includes a sidewall 82 that extends upwardly on the inner side 22 as well as on the outer side 26. As best seen in FIGS. 1 and 3, as the sidewall 82 extends rearwardly toward the heel cup portion 66, it increases in height to surround the heel and form a well. The side wall 82 also provides a means for positioning the foot 14 within the foot pad 46 during use of the device 10.

One of the most common ways freezer burn or mild frost bite occurs is through the application of an ice pack to an injury. Referring now to FIGS. 3 and 4, a protective layer 80 is arranged to lie over the upper foot bed 62 to provide a layer of protection between the bottom surface of the foot 14 and the cold surface of the upper foot bed 62 to prevent damage to the skin, e.g., freezer burn or mild frost bite, due to direct contact of the skin with the cold surface of the upper foot bed 62. The protective layer 80 is contoured to fit within the sidewall 82 and extends upwardly at the back of the heel 18 to provide a layer of protection between the thickened portion 70 and the wearer's heel in proximity to the Achilles' tendon 72 to prevent such cold burns in this area. The protective layer 80 may be fabricated of a thin fabric material, for example, a fabric that is used for covering an insole of a shoe or sneaker.

Prior to use, the device 10 may be placed in a freezer to enable the coolant or refrigerant 54 located within the container to solidify. Once the refrigerant 54 has solidified, the resulting foot pad 46 is cold and rigid.

Thereafter, the foot pad 46 may be engaged to the bottom surface of the foot in any conventional manner, such as, by way of example, straps 90, 94, and 98, with cooperating hook and loop fasteners 100 and 104 (FIG. 2), e.g., VELCRO® brand fasteners. (VELCRO® is a registered trademark of Velcro Industries, B.V.).

In this manner, the foot pad 46 serves as a rigid cold compress for application against the bottom surface of the foot. The foot pad 46 is contoured to the shape of the bottom of the foot including the heel, the ball area, and the arch. In this manner, cold therapy may be provided to the bottom of the foot to alleviate pain and inflammation associated with plantar fasciitis and tendonitis. Likewise, the thickened portion 70 integral with the recessed heel cup portion 66 extends upwardly to make contact with the wearer's heel in proximity to the wearer's Achilles' tendon 72 to provide cold therapy at that location, as Achilles tendonitis often accompanies plantar fasciitis. The foot pad 46 may be brought into tight engagement with the bottom surface of the foot by suitably tightening the straps 90, 94, and 98, as required. The device 10 is reusable in that after therapy has been provided, the device 10 may be returned to the freezer or other cooling system to lower its temperature for reuse.

Various alternative coolants or refrigerants 54 may be injected through the outer wall 50 of the foot pad 46. The coolant or refrigerant 54 may be inserted into the foot pad 46 through a port 108 located in proximity to the rearward thickened portion 70 of the recessed heel cup portion 66. The coolants or refrigerants may be non-toxic, e.g., ice. Alternatively, gels made of non-toxic materials that will not liquefy, and therefore will not spill easily or cause contamination if the foot pad 46 breaks may be utilized. Such gels may be made from hydroxyethyl cellulose (Cellusize) or vinyl-coated silica gel, or other suitable materials. These gels, as with ice itself, are chilled before use. The foot pad 46 is placed in a freezer or other cooling system to lower its temperature, and then it may be used to apply cold therapy to regions of the foot where inflammation occurs such as the plantar fascia and tendons of the foot including the Achilles tendon. The coolness of the foot pad 46 will reduce inflammation and reduce sensations of pain and tenderness.

While various embodiments have been shown and described, various modifications and substitutions may be made thereto without departing from the spirit and scope of the invention.

I claim:

1. A device for applying cold therapy to the foot of a wearer, the foot having a heel, an arch, a metatarsal region, and toes, said device comprising:

a. a foot pad in the form of a reusable freezer pack having a rigid premolded configuration for directly contacting the bottom of the foot in a frozen state and comprising a heel cup sized to surround the heel of the foot, a raised and contoured arch portion positioned to lie beneath and place localized pressure on the arch of the foot, said reusable freezer pack including a shell containing a substance capable of maintaining an extremely low temperature for an extended period of time during application to the foot said foot pad being a unitary structure; and b. a securement mechanism arranged for engaging said foot pad to the bottom of the wearer's foot, said device adapted to be used while the wearer is not standing.

2. The device of claim 1, wherein said foot pad is comprised of a contiguous outer wall formed of an impervious material.

3. The device of claim 1, wherein said foot pad comprises interconnecting medial, lateral, and heel sidewalls that together form a peripheral wall, and wherein said securement mechanism comprises a plurality of attachment straps arranged for securement to said foot pad.

4. The device of claim 2, wherein said plurality of attachment straps comprises three attachment straps, a first strap arranged for wrapping around the wearer's ankle, the second and third straps arranged for wrapping around the wearer's foot.

5. The device of claim 1, wherein said substance contained within said shell is selected from the group consisting of a frozen gel, a frozen liquid, dry ice, or a frozen silicon gel.

6. The device of claim 1, wherein said foot pad extends from said heel cup across said arch portion to a location of the foot just beneath the metatarsal region.

7. The device of claim 1, wherein said device is reusable.

8. The device of claim 1, wherein said device is intended to be worn intermittently.

9. The device of claim 1, further comprising a front edge located just beneath the metatarsal region of the foot.

10. The device of claim 9, wherein said front edge is rounded.

11. The device of claim 1, wherein said foot pad additionally comprises an upwardly extending thickened portion positioned to make contact with the wearer's Achilles' tendon to provide cold therapy thereto.

12. The device of claim 1, additionally comprising a protective layer arranged to be situated over said foot pad.

13. The device of claim 12, wherein said protective layer is formed of a fabric material glued to said foot pad.

* * * * *